US011319498B2

(12) United States Patent
Goyheneix et al.

(10) Patent No.: US 11,319,498 B2
(45) Date of Patent: May 3, 2022

(54) OPTIMIZING THE SIMULTANEOUS PRODUCTION OF HIGH-VALUE CHEMICALS AND FUELS FROM HEAVY HYDROCARBONS

(71) Applicants: SABIC Global Technologies B.V., Bergen op Zoom (NL); SAUDI ARABIAN OIL COMPANY, Dhahran (SA)

(72) Inventors: Nicolas Goyheneix, Riemst (BE); Hatem Belfadhel, Riyadh (SA); Jurgen Kleibergen, Geleen (NL); Vinod Ramaseshan, Dhahran (SA); Timothy Abbott, Redcar (GB); Mohamed Sabri Abdelghani, Riyadh (SA)

(73) Assignees: SABIC GLOBAL TECHNOLOGIES B.V., Bergen op Zoom (NL); SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 17/299,108

(22) PCT Filed: Dec. 3, 2019

(86) PCT No.: PCT/IB2019/060405
§ 371 (c)(1),
(2) Date: Jun. 2, 2021

(87) PCT Pub. No.: WO2020/115659
PCT Pub. Date: Jun. 11, 2020

(65) Prior Publication Data
US 2022/0056355 A1 Feb. 24, 2022

Related U.S. Application Data

(60) Provisional application No. 62/775,241, filed on Dec. 4, 2018.

(51) Int. Cl.
| | |
|---|---|
| C07C 41/06 | (2006.01) |
| C10G 7/06 | (2006.01) |
| C10G 9/00 | (2006.01) |
| C10G 47/12 | (2006.01) |
| C10G 49/04 | (2006.01) |
| C10G 57/00 | (2006.01) |
| C10G 69/06 | (2006.01) |
| C10G 69/14 | (2006.01) |
| C10G 55/04 | (2006.01) |
| C10G 67/04 | (2006.01) |

(52) U.S. Cl.
CPC ............ *C10G 69/14* (2013.01); *C10G 55/04* (2013.01); *C10G 67/049* (2013.01)

(58) Field of Classification Search
CPC .. C07C 41/06; C10G 7/06; C10G 9/00; C10G 21/003; C10G 47/12; C10G 49/04; C10G 57/00; C10G 67/049; C10G 69/06
See application file for complete search history.

(56) References Cited

U.S. PATENT DOCUMENTS

| | | | |
|---|---|---|---|
| 3,993,457 A | 11/1976 | Cahn et al. | |
| 4,039,429 A | 8/1977 | Van Klinken et al. | |
| 4,391,701 A | 7/1983 | Le Page et al. | |
| 4,810,417 A | 3/1989 | Diemer et al. | |
| 6,419,399 B1 | 7/2002 | Loder et al. | |
| 7,964,090 B2 | 6/2011 | Iqbal | |
| 8,721,927 B2 | 5/2014 | Koseoglu | |
| 2011/0259014 A1 | 10/2011 | Miller et al. | |
| 2013/0319910 A1 | 12/2013 | Koseoglu et al. | |
| 2015/0038599 A1 | 2/2015 | Kresnyak | |
| 2016/0368848 A1 | 12/2016 | Axelrod et al. | |
| 2018/0155639 A1 | 6/2018 | Al-Ghamdi et al. | |

(Continued)

FOREIGN PATENT DOCUMENTS

| | | |
|---|---|---|
| AU | 2001255384 A1 | 2/2002 |
| CA | 1205632 A | 6/1986 |
| CN | 1179023 A | 4/1998 |

(Continued)

OTHER PUBLICATIONS

Bernetti et al. "Solvent deasphalting and gasification: a synergy." www.digitalrefining.com/article/1000690. 2000. 7 pages.
Furimsky, E. "Gasification in Petroleum Refinery of 21st Century." Oil & Gas Science and Technology—Rev. IFP, vol. 54 (1999), No. 5, 597-618.
International Search Report and Written Opinion from PCT/IB2019/060405 dated Jan. 24, 2020, 13 pages.
Jechura, John. "Bottom of Barrel Processing." Colorado School of Mines. Jan. 26, 2016. Chapters 5, 6, & 8. 18 pages.
Lei, Y. et al. "Gasification of n-C7 asphaltenes using Ni-based catalysts." Petroleum Science and Technology, 35:24, (2017) 2283-2286, DOI: 10.1080/10916466.2017.1402033.

(Continued)

*Primary Examiner* — Randy Boyer
(74) *Attorney, Agent, or Firm* — Norton Rose Fulbright US LLP (57) ABSTRACT

Methods and systems for producing light olefins are disclosed. A feedstock comprising crude oil is distilled to produce a plurality of streams including a naphtha stream and a vacuum residue stream. The naphtha is fed to a steam cracking unit to produce light olefins, $C_4$ hydrocarbons, pyrolysis gasoline and pyrolysis oil. The vacuum residue stream is hydrocracked to produce additional naphtha and heavy unconverted oil. The heavy unconverted oil and the pyrolysis oil from steam cracking unit can be deasphalted to produce deasphalted oil and pitch product. The deasphalted oil can be further hydrocracked to produce naphtha. The pitch product can be gasified to produce synthesis gas, which is further used to produce methanol. The methanol can be used to react with isobutylene of the $C_4$ hydrocarbon stream from steam cracker to produce methyl tert-butyl ether (MTBE).

20 Claims, 3 Drawing Sheets

(56) References Cited

U.S. PATENT DOCUMENTS

2018/0155643 A1* 6/2018 Al-Ghamdi ............. C10G 7/06

FOREIGN PATENT DOCUMENTS

| CN | 1179023 C | 2/2002 |
|---|---|---|
| EP | 0372652 A1 | 6/1990 |
| EP | 1313824 A1 | 5/2003 |
| EP | 1114126 B1 | 9/2004 |
| EP | 2737031 A1 | 6/2014 |
| WO | WO2009003633 A1 | 1/2009 |
| WO | WO2009003634 A1 | 1/2009 |
| WO | WO2013043443 A1 | 3/2013 |
| WO | WO2018122274 A1 | 7/2018 |

OTHER PUBLICATIONS

Mahapatra, Nirlipt. "Pyrolysis of asphaltenes in an atmospheric entrained flow reactor: A study on gasification reactivity and properties of chars." University of Alberta, Department of Chemical and Materials Engineering, Thesis, 2014, 110 pages.

Moretta et al. "Refinery residuals as a source of chemical feedstock refinery residuals as a source of chemical feedstock." World Petroleum Congress. 16th World Petroleum Congress, Jun. 11-15, Calgary, Canada. 2000. 7 pages.

Mukherjee, Ujjal. "Advanced Residue Hydrocracking." Chevron Lummus Global, 2015, 52 pages.

* cited by examiner

FIG. 2

OPTIMIZING THE SIMULTANEOUS PRODUCTION OF HIGH-VALUE CHEMICALS AND FUELS FROM HEAVY HYDROCARBONS

CROSS REFERENCE TO RELATED APPLICATIONS

This application is a national phase application under 35 U.S.C. § 371 of International Application No. PCT/IB2019/060405 filed Dec. 3, 2019, which claims priority to U.S. Provisional Patent Application No. 62/775,241 filed Dec. 4, 2018. The entire contents of each of the above-referenced disclosures is specifically incorporated by reference herein without disclaimer.

FIELD OF INVENTION

The present invention generally relates to integrated processes for hydroprocessing vacuum residue obtained from distilling crude oil and pyrolysis oil obtained from steam cracking hydrocarbons. More specifically, the present invention relates to an integrated process that includes hydroprocessing both vacuum residue and a deasphalted pyrolysis oil in a hydrocracking unit and processing pitch product obtained in the deasphalting process to produce synthesis gas.

BACKGROUND OF THE INVENTION

Light olefins ($C_2$ to $C_3$ olefins) are building blocks for many chemical processes. Light olefins are used to produce polyethylene, polypropylene, ethylene oxide, ethylene chloride, propylene oxide, and acrylic acid, which, in turn, are used in a wide variety of industries such as the plastic processing, construction, textile, and automotive industries.

BTX (benzene, toluene, and xylene) are a group aromatics that are used in many different areas of the chemical industry, especially the plastic and polymer sectors. For instance, benzene is a precursor for producing polystyrene, phenolic resins, polycarbonate, and nylon. Toluene is used for producing polyurethane and as a gasoline component. Xylene is feedstock for producing polyester fibers and phthalic anhydride.

Conventionally, light olefins and BTX is produced by steam cracking naphtha. However, naphtha is merely one of many fractions from crude oil. As the demand for light olefins and BTX have been consistently increasing, more feedstocks are needed for producing these chemicals. Furthermore, steam cracking of naphtha generally has high operating costs. One of the reasons for the high operating costs include that heavy byproducts produced by steam cracking including $C_9$+ hydrocarbons, carbon black oil, and cracked distillates are merely used as low-value fuel.

Overall, while methods of producing light olefins and BTX via hydrocarbon stream upgrading exist, the need for improvements in this field persists in light of at least the aforementioned drawbacks for the methods.

BRIEF SUMMARY OF THE INVENTION

A solution to at least some of the above-mentioned problems associated with producing light olefins and BTX via steam cracking naphtha has been discovered. The solution resides in a method of producing light olefins that includes hydrocracking vacuum residue from crude oil distillation and pyrolysis oil from steam cracking hydrocarbons to produce naphtha, which is further steam cracked to produce light olefins. This can be beneficial for fully utilizing pyrolysis oil to produce high-value products including light olefins and BTX as pyrolysis oil is conventionally used as low-value fuel oil. Furthermore, the unconverted oil produced by hydrocracking vacuum residue and/or pyrolysis oil can be deasphalted to produce deasphalted oil and pitch product. The deasphalted oil can be further hydrocracked to produce naphtha, resulting in an improved conversion rate of heavy hydrocarbons. The pitch product can be gasified to produce synthesis gas, resulting in high utilization rate of low-value hydrocarbon stream. Therefore, the method of the present invention provides a technical solution over at least some of the problems associated with the currently available methods of upgrading heavy hydrocarbon streams for light olefin production mentioned above.

Embodiments of the invention include a method of producing olefins. The method comprises distilling a feedstock comprising crude oil to produce a plurality of distilling product streams comprising a naphtha stream and a vacuum residue stream. The method further comprises steam cracking the naphtha stream to produce a plurality of cracking product streams comprising a $C_2$ to $C_3$ olefins stream, a $C_4$ hydrocarbon mixture stream, and a pyrolysis oil stream. The method further comprises hydrocracking the vacuum residue stream to produce a distillate stream having a boiling range less than the vacuum residue stream and a heavy unconverted oil stream having a boiling range higher than the vacuum residue stream. The method further still comprises deasphalting the heavy unconverted oil stream and the pyrolysis oil from steam-cracking with a solvent to produce a deasphalted oil stream and a pitch stream.

Embodiments of the invention include a method of producing olefins. The method comprises distilling a feedstock comprising crude oil to produce a plurality of distilling product streams comprising a naphtha stream and a vacuum residue stream. The method further comprises steam cracking the naphtha stream to produce a plurality of cracking product streams comprising a $C_2$ to $C_3$ olefins stream, a $C_4$ hydrocarbon mixture stream, and a pyrolysis oil stream. The method further comprises hydrocracking the vacuum residue stream to produce a distillate stream having a boiling range less than the vacuum residue stream and a heavy unconverted oil stream having a boiling range higher than the vacuum residue stream. The method further still comprises deasphalting the heavy unconverted oil stream and the pyrolysis oil from steam-cracking with a solvent to produce a deasphalted oil stream and a pitch stream. The method further comprises gasifying the pitch stream to produce a synthesis gas stream.

Embodiments of the invention include a method of producing olefins. The method comprises distilling a feedstock comprising crude oil to produce a plurality of distilling product streams comprising a naphtha stream and a vacuum residue stream. The method further comprises steam cracking the naphtha stream to produce a plurality of cracking product streams comprising a $C_2$ to $C_3$ olefins stream, a $C_4$ hydrocarbon mixture stream, and a pyrolysis oil stream. The method further comprises hydrocracking the vacuum residue stream to produce a distillate stream having a boiling range less than the vacuum residue stream and a heavy unconverted oil stream having a boiling range higher than the vacuum residue stream. The method further still comprises deasphalting the heavy unconverted oil stream and the pyrolysis oil from steam-cracking with a solvent to produce a deasphalted oil stream and a pitch stream. The method further comprises gasifying the pitch stream to produce a synthesis gas stream. The method further comprises hydrocracking the deasphalted oil stream to produce naphtha. The method further comprises reacting carbon monoxide and hydrogen of the synthesis gas stream to produce at least some methanol. The method further comprises reacting the methanol with isobutylene from the $C_4$ hydrocarbon mixture stream under reaction conditions sufficient to produce MTBE.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The term "crude oil," as that term is used in the specification and/or claims, refers to an unrefined petroleum product having naturally occurring hydrocarbons and other organic materials. An "unrefined petroleum product," in this context, means a petroleum product that has not been subjected to a distillation process to produce products such as gasoline, naphtha, kerosene, gasoil, and residue. Refining in this context does not include pre-treatment of crude oil that does not make such products. Thus, crude oil, as used herein, includes petroleum products that have been subjected to a selection from water-oil separation, gas-oil separation, desalting, stabilization, and combinations thereof.

The term "vacuum gas oil," as that term is used in the specification and/or claims, refers to hydrocarbons that having a boiling range of 360 to 550° C., 360 to 540° C., 360 to 530° C., 360 to 510° C., 400 to 550° C., 400 to 540° C., 400 to 530° C., 400 to 510° C., 420 to 550° C., 420 to 540° C., 420 to 530° C., or 420 to 510° C.

The term "pyrolysis oil," and its abbreviated form "py-oil," as used in the specification and/or claims, refers to a heavy hydrocarbon fraction containing $C_9$+ hydrocarbons derived from steam cracking hydrocarbons.

The term "pyrolysis gasoline" and its abbreviated form "py-gas," as used in the specification and/or claims refer to a $C_5$ to $C_9$ hydrocarbon fraction derived from thermal cracking products including steam cracking of hydrocarbons.

The term "vacuum residue," as that term is used in the specification and/or claims, refers to the asphaltene-containing portion of unconverted oil from hydroprocessed vacuum residue after de-asphalting process.

The term "pitch," as that term is used in the specification and/or claims, refers to the asphaltene-containing portion of unconverted oil from hydroprocessed vacuum residue after the deasphalting process.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

Currently, light olefins can be produced by steam cracking naphtha obtained from distillation of crude oil. However, more feedstocks for producing light olefins are needed as the demand for light olefins has been consistently increasing. Furthermore, steam cracking naphtha generally has a high operating cost partially because byproducts from steam cracking naphtha, including pyrolysis oil, is conventionally used as low-value fuel oil. The present invention provides a solution to at least some of these problems. The solution is premised on a method that comprises hydrocracking both vacuum residue from crude oil distillation and deasphalted pyrolysis oil from steam cracking naphtha to produce at least some additional naphtha, which can be used as additional feedstock for steam cracking. Furthermore, unconverted oil produced in the hydrocracking process can be further deasphalted to produce deasphalted oil, which can be recycled to the hydrocracking process. The pitch produced during the deasphalting process can be used to produce synthesis gas, which can be further converted to methanol. The methanol production process can be further integrated with an MTBE production unit, which uses isobutylene produced from steam cracking naphtha and the methanol to produce MTBE. Overall, this method is capable of improving the utilization rate of heavy hydrocarbon streams including vacuum residue and/or pyrolysis oil by integrating multiple refinery/petrochemical processes, thereby reducing production costs for olefins and other petrochemicals. These and other non-limiting aspects of the present invention are discussed in further detail in the following sections.

A. System for Producing Light Olefins

Figure 1A:
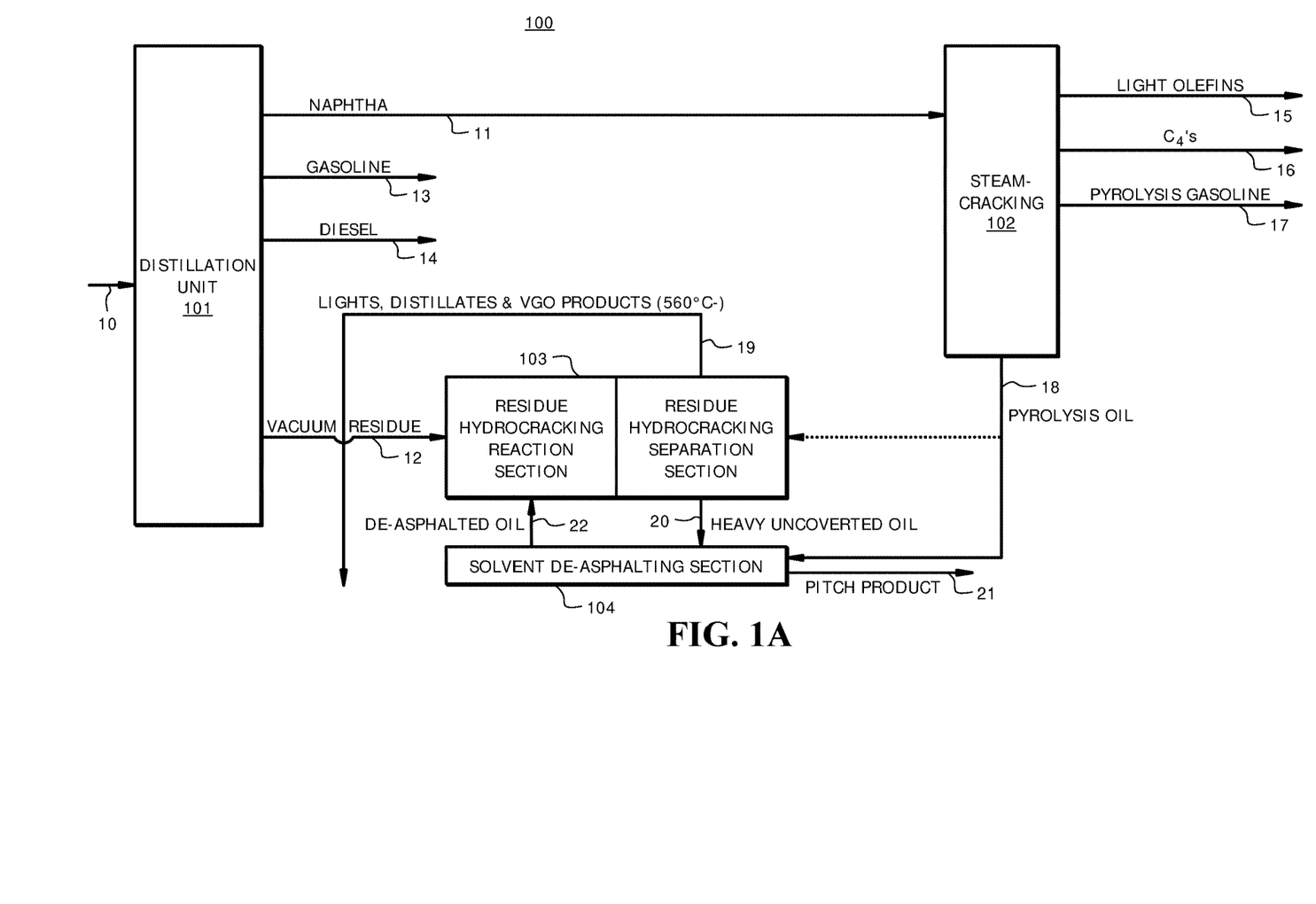
FIG. 1A shows a schematic diagram of a system for producing light olefins, according to embodiments of the invention.

In embodiments of the invention, the system for producing light olefins includes an integrated system for distilling crude oil, hydrocracking vacuum residue and pyrolysis oil, steam cracking naphtha, and producing MTBE using isobutylene from the steam cracking. With reference to FIG. 1A, a schematic diagram is shown of system 100 that is capable of producing light olefins using feedstocks produced by upgrading heavy hydrocarbons streams from refinery/petrochemical processes. According to embodiments of the invention, system 100 may include distillation unit 101 configured to separate hydrocarbon feed stream 10 including crude oil into a plurality of streams. In embodiments of the invention, the plurality of streams may include naphtha stream 11 and vacuum residue stream 12. The plurality of streams may further include gasoline stream 13 and diesel stream 14. In embodiments of the invention, distillation unit 101 may comprise an atmospheric distillation column, a vacuum distillation, or combinations thereof.

In embodiments of the invention, a first outlet of distillation unit 101 may be in fluid communication with steam cracking unit 102 such that naphtha stream 11 flows from distillation unit 101 to steam cracking unit 102. According to embodiments of the invention, steam cracking unit 102 may be adapted to crack naphtha under reaction conditions sufficient to produce at least some light olefins (e.g., ethylene and propylene). In embodiments of the invention, effluent from steam cracking unit 102 may be separated into light olefins stream 15, $C_4$ hydrocarbon stream 16, pyrolysis gasoline stream 17, pyrolysis oil stream 18, or combinations thereof.

In embodiments of the invention, a second outlet of distillation unit 101 may be in fluid communication with an inlet of hydrocracking unit 103 such that vacuum residue stream 12 flows from distillation unit 101 to hydrocracking unit 103. In embodiments of the invention, hydrocracking unit 103 may be adapted to hydrocrack vacuum residue of vacuum residue stream 12 in the presence of a catalyst under reaction conditions sufficient to produce at least some light distillate. In embodiments of the invention, the light distillate may comprise at least some naphtha. According to embodiments of the invention, effluent from hydrocracking unit 103 may further include vacuum gas oil, liquefied petroleum gas, middle distillate (including hydrocarbons in the boiling range of gasoil), unconverted oil, or combinations thereof. In embodiments of the invention, the catalyst of hydrocracking unit 103 may include various transition metals, or metal sulfides with a solid support comprising alumina, silica, alumina-silica, magnesia and zeolites, or combinations thereof.

According to embodiments of the invention, hydrocracking unit 103 may include a (i) hydrocracking reaction section comprising one or more hydrocrackers and (ii) a hydrocracking separation section adapted to separate effluent from hydrocracking reaction section into distillate stream 19 and heavy unconverted oil stream 20. In embodiments of the invention, a first outlet of hydrocracking separation section may be in fluid communication with an inlet of a separation unit that is adapted to further separate distillate stream 19 such that distillate stream 19 flows from hydrocracking separation section to the separation unit. In embodiments of the invention, the separation unit may be distillation unit 101. Distillate stream 19 may include light distillate, middle distillate, vacuum gasoil, or combinations thereof. In embodiments of the invention, a second outlet of hydrocracking separation section may be in fluid communication with deasphalting unit 104 such that heavy-unconverted oil stream 20 flows from hydrocracking separation section to deasphalting unit 104. In embodiments of the invention, heavy unconverted oil stream 20 comprises unconverted oil from hydrocracking unit 103.

According to embodiments of the invention, an outlet of steam cracking unit 102 may be in fluid communication with deasphalting unit 104 such that at least a portion of pyrolysis oil stream 18 flows from steam cracking unit 102 to deasphalting unit 104. Alternatively or additionally, the outlet of steam cracking unit 102 may be in fluid communication with an inlet of hydrocracking separation section such that at least a portion of pyrolysis oil stream 18 flows from steam cracking unit 102 to hydrocracking separation section. In embodiments of the invention, deasphalting unit 104 may be adapted to separate asphalt from unconverted oil and/or pyrolysis oil to form streams including pitch product stream 21, and/or deasphalted oil stream 22. In embodiments of the invention, deasphalting unit 104 may comprise a solvent deasphalting unit.

In embodiments of the invention, a first outlet of deasphalting unit 104 may be in fluid communication with hydrocracking unit 103 such that deasphalted oil stream 22 flows from deasphalting unit 104 to hydrocracking unit 103. Hydrocracking unit 103 may be further adapted to hydrocrack deasphalted oil stream 22 to produce additional light distillate, middle distillate, vacuum gasoil, unconverted oil, or combinations thereof. In embodiments of the invention, as shown FIG. 1B, a second outlet of deasphalting unit 104 may be in fluid communication with gasification unit 105 such that pitch product stream 21 flows from deasphalting unit 104 to gasification unit 105. According to embodiments of the invention, gasification unit 105 may be adapted to react pitch product under reaction conditions sufficient to gasify pitch product and produce at least some synthesis gas. In embodiments of the invention, an outlet of gasification unit 105 may be in fluid communication with methanol plant 106 such that synthesis gas stream 23 flows from gasification unit 105 to methanol plant 106.

Figure 1B:
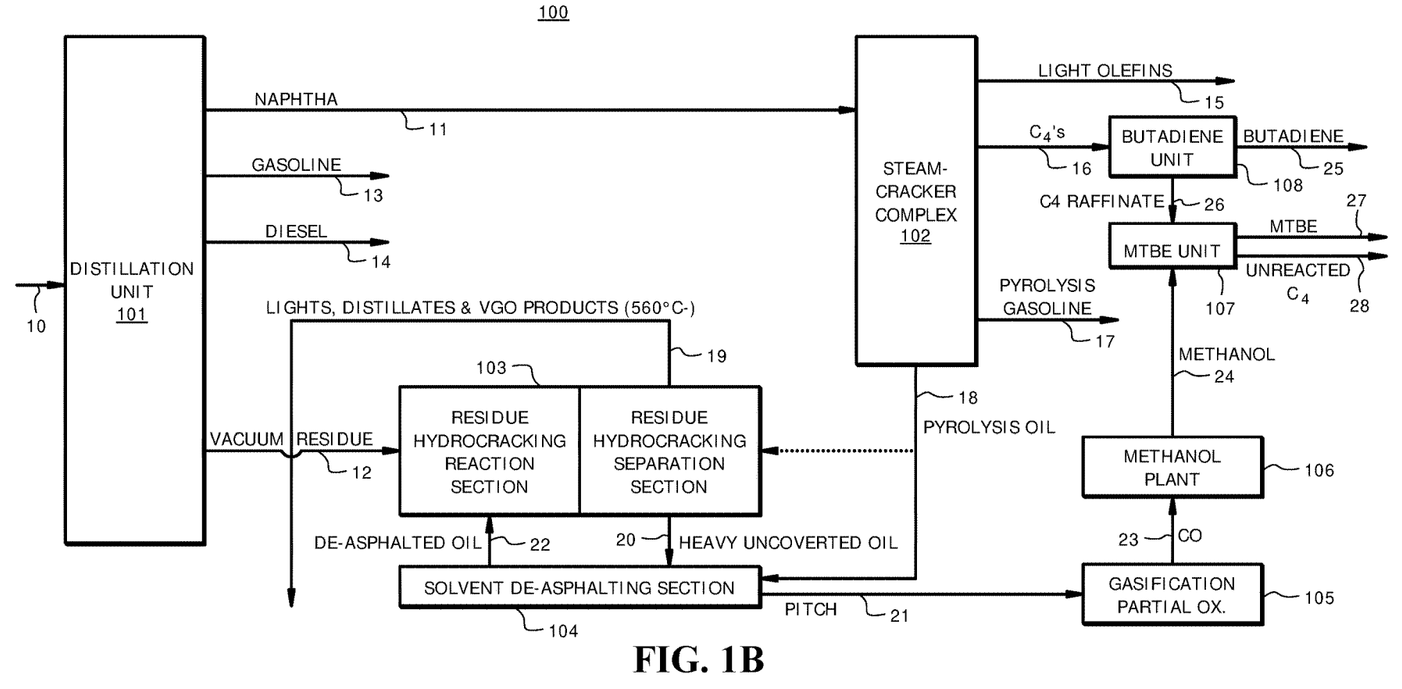
FIG. 1B shows a schematic diagram of a system for producing light olefins integrated with an MTBE unit, according to embodiments of the invention.

According to embodiments of the invention, methanol plant 106 may be adapted to react carbon monoxide and hydrogen of synthesis gas stream 23 in the presence of a catalyst under reaction conditions sufficient to produce at least some methanol. In embodiments of the invention, methanol plant 106 may be further adapted to purify synthesis gas stream 23 and adjust the ratio between carbon monoxide and hydrogen of synthesis gas stream 23 for methanol production before the reaction of carbon monoxide and hydrogen. In embodiments of the invention, the catalyst for catalyzing the production of methanol from synthesis gas may include metal or metal oxides including copper, zinc, other transition metals, or oxides thereof supported on a solid support including alumina, silicates, or combinations thereof.

In embodiments of the invention, an outlet of methanol plant 106 may be in fluid communication with MTBE unit 107 such that methanol stream 24 flows from methanol plant 106 to MTBE unit 107. According to embodiments of the invention, an outlet of steam cracking unit 102 may be in fluid communication with butadiene unit 108 such that $C_4$ hydrocarbon stream 16 flows from steam cracking unit 102 to butadiene unit 108. In embodiments of the invention, butadiene unit 108 may be adapted to separate butadiene from $C_4$ hydrocarbon stream 16 to form butadiene stream 25 comprising primarily butadiene, and $C_4$ raffinate stream 26 comprising n-butane, isobutane, 1-butene, 2-butene, isobutylene, or combinations thereof. In embodiments of the invention, butadiene unit 108 may include one or more extraction units In embodiments of the invention, an outlet of butadiene unit 108 may be in fluid communication with MTBE unit 107 such that $C_4$ raffinate stream 26 flows from butadiene unit 108 to MTBE unit 107. According to embodiments of the invention, MTBE unit 107 may be adapted to react isobutylene of $C_4$ raffinate stream 26 with methanol of methanol stream 24 in the presence of a catalyst under reaction conditions to produce MTBE stream 27 and unreacted $C_4$ stream 28. In embodiments of the invention, the catalyst adapted to catalyze production of MTBE from isobutylene and methanol may include weakly or strongly acidic ion exchange resins incorporated with acid groups comprising one or more sulfonic groups and/or one or more carboxylic groups.

B. Method of Producing Light Olefins

Figure 2:
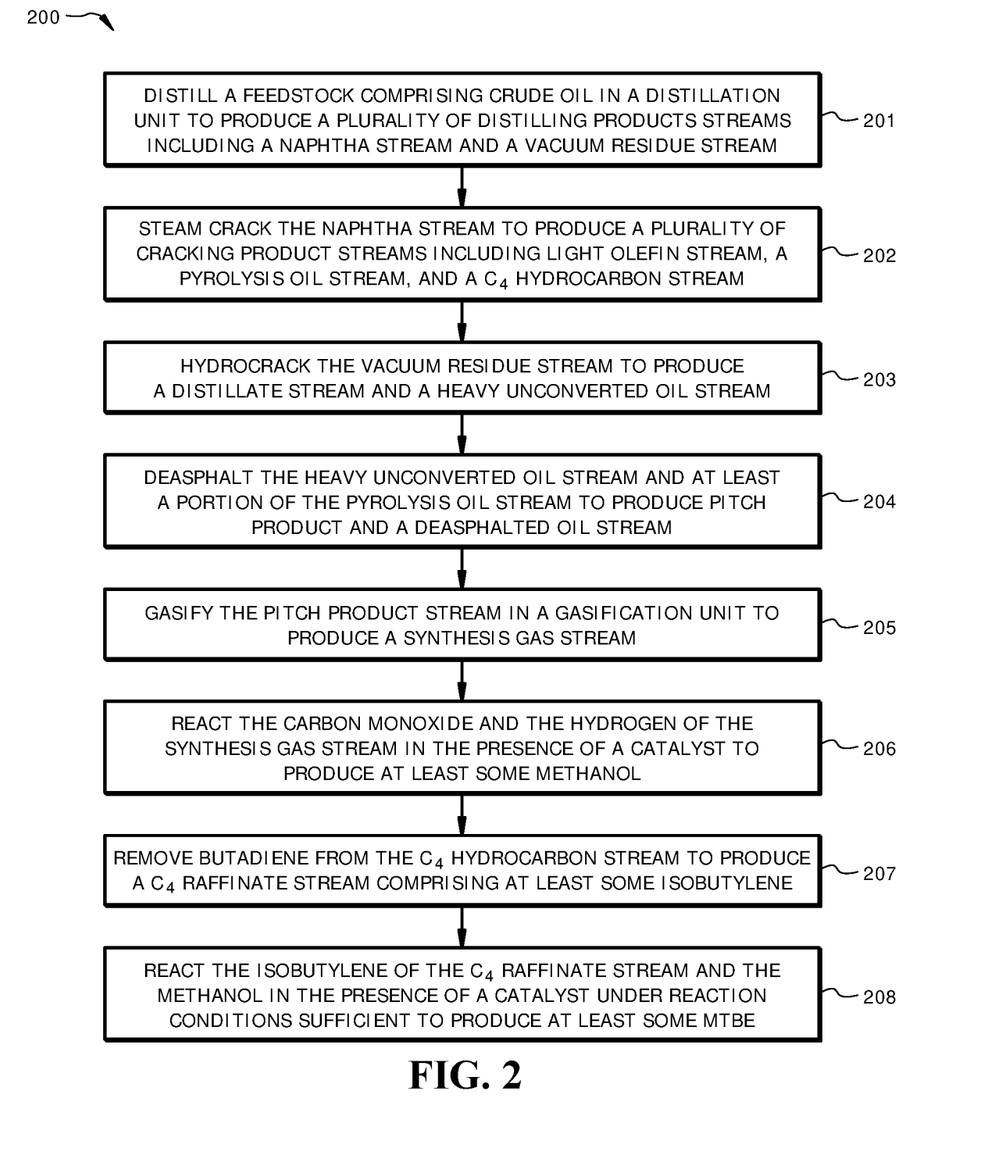
FIG. 2 shows a schematic flowchart of a method of producing light olefins, according to embodiments of the invention.

Methods of producing light olefins have been discovered. The methods may include upgrading heavy hydrocarbons from refinery/petrochemical processes to provide additional feedstock for producing light olefins via steam cracking. Furthermore, the methods may integrate processes to fully utilize heavy hydrocarbons produced in various refinery/petrochemical units, resulting in reduced production cost for light olefins and/or other petrochemicals. As shown in FIG. 2, embodiments of the invention include method 200 for producing light olefins. Method 200 may be implemented by system 100, as shown in FIGS. 1A and 1B. According to embodiments of the invention, as shown in block 201, method 200 may comprise distilling, in distillation unit 101, a feedstock comprising crude oil to produce a plurality of distilling product streams. In embodiments of the invention, the distilling product streams may include naphtha stream 11 and vacuum residue stream 12. In embodiments of the invention, the distilling product streams may further include gasoline stream 13 and/or diesel stream 14. In embodiments of the invention, the distilling at block 201 may be carried out at an overhead boiling range of 80 to 200° C. and a reboiler boiling range of 300 to 450° C. The distilling at block 201 may be carried at a pressure of 1 to 10 bar and all ranges and values there between including 2 bar, 3 bar, 4 bar, 5 bar, 6 bar, 7 bar, 8 bar, and 9 bar.

According to embodiments of the invention, as shown in block 202, method 200 may further include steam cracking naphtha stream 11 in steam cracking unit 102 to produce a plurality of cracking product streams. In embodiments of the invention, the cracking product streams may include light olefin stream 15, $C_4$ hydrocarbon mixture stream 16, pyrolysis oil stream 18, or combinations thereof. In embodiments of the invention, the cracking product streams may further include pyrolysis gasoline stream 17. According to embodiments of the invention, steam cracking at block 202 may be carried out at a temperature of 750 to 950° C. and all ranges and values there between including ranges of 750 to 760° C., 760 to 770° C., 770 to 780° C., 780 to 790° C., 790 to 800° C., 800 to 810° C., 810 to 820° C., 820 to 830° C., 830 to 840° C., 840 to 850° C., 850 to 860° C., 860 to 870° C., 870 to 880° C., 880 to 890° C., 890 to 900° C., 900 to 910° C., 910 to 920° C., 920 to 930° C., 930 to 940° C., and 940 to 950° C. The steam cracking at block 202 may be carried out with a steam to hydrocarbon weight ratio of 0.1 to 1 and all ranges and values there between including 0.2, 0.3, 0.4, 0.5, 0.6, 0.7, 0.8, and 0.9. A residence time for steam cracking unit 102 at block 202 may be in a range of 50 to 1000 ms and all ranges and values there between, including 50 to 100 ms, 100 to 200 ms, 200 to 300 ms, 300 to 400 ms, 400 to 500 ms, 500 to 600 ms, 600 to 700 ms, 700 to 800 ms, 800 to 900 ms, and 900 to 1000 ms. In embodiments of the invention, light olefin stream 15 may include 5 to 80 wt. % ethylene and 1 to 30 wt. % propylene. $C_4$ hydrocarbon mixture stream 16 may include n-butane, isobutane, isobutylene, 1-butene, 2-butene, butadiene, or combinations thereof. Pyrolysis oil stream 18 may include benzene, toluene, xylenes, or combinations thereof.

According to embodiments of the invention, as shown in block 203, method 200 may further include hydrocracking vacuum residue stream 12 to produce distillate stream 19 having a boiling range less than vacuum residue stream and heavy unconverted oil stream 20 having a boiling range higher than vacuum residue stream 12. In embodiments of the invention, hydrocracking at block 203 may be carried out at a reaction temperature of 300 to 500° C. and all ranges and values there between, including 300 to 325° C., 325 to 350° C., 350 to 375° C., 375 to 400° C., 400 to 425° C., 425 to 450° C., 450 to 475° C. and 475 to 500° C. A reaction pressure for hydrocracking at block 203 may be in a range of 10 to 250 bar and all ranges and values there between, including 10 to 25 bar, 25 to 50 bar, 50 to 75 bar, 75 to 100 bar, 100 to 125 bar, 125 to 150 bar, 150 to 175 bar, 175 to 200 bar, 200 to 225 bar, and 225 to 250 bar. In embodiments of the invention, hydrocracking at block 203 may be carried out at a hydrogen to hydrocarbon volumetric ratio of 50 to 1000 and all ranges and values there between, including 50 to 100, 100 to 200, 200 to 300, 300 to 400, 400 to 500, 500 to 600, 600 to 700, 700 to 800, 800 to 900, and 900 to 1000. In embodiments of the invention, distillate stream 19 may be separated in a separation unit to produce at least some naphtha, middle distillate, vacuum gas oil, or combinations thereof. In embodiments of the invention, one or more of the naphtha, middle distillate, vacuum gas oil produced from separating distillate stream 19 may be cracked in steam cracking unit 102 to produce additional light olefins, additional mixed $C_4$ hydrocarbons, additional pyrolysis gasoline, additional pyrolysis oil, or combinations thereof.

According to embodiments of the invention, as shown in block 204, method 200 may further include deasphalting heavy unconverted oil stream 20 and/or at least a portion of pyrolysis oil stream 18 from steam cracking unit 102 in deasphalting unit 104 with a solvent to produce deasphalted oil stream 22 and pitch product stream 21. In embodiments of the invention, the solvent may include propane, pentane, butane, or combinations thereof. As an alternative to or in addition to flowing a portion of pyrolysis oil stream to deasphalting unit 104, a portion of pyrolysis oil stream 18 may be flowed to the separation section of hydrocracking unit 103 to produce additional heavy unconverted oil and/or additional distillate stream 19. The additional heavy unconverted oil may be further deasphalted in deasphalting unit 104.

According to embodiments of the invention, as shown in block 205, method 200 may further comprise gasifying pitch product stream 21 in gasification unit 105 to produce synthesis gas stream 23 comprising primarily carbon monoxide and hydrogen, collectively. In embodiments of the invention, gasifying at block 205 may be carried out at a temperature of 700 to 1500° C. and all ranges and values there between, including 700 to 750° C., 750 to 800° C., 800 to 850° C., 850 to 900° C., 900 to 950° C., 950 to 1000° C., 1000 to 1050° C., 1050 to 1100° C., 1100 to 1150° C., 1150 to 1200° C., 1200 to 1250° C., 1250 to 1300° C., 1300 to 1350° C., 1350 to 1400° C., 1400 to 1450° C., and 1450 to 1500° C. A reaction pressure of gasification at block 205 may be in a range of 1 to 60 bar and all ranges and values there between, including 1 to 5 bar, 5 to 10 bar, 10 to 15 bar, 15 to 20 bar, 20 to 25 bar, 25 to 30 bar, 30 to 35 bar, 35 to 40 bar, 40 to 45 bar, 45 to 50 bar, 50 to 55 bar, and 55 to 60 bar. In embodiments of the invention, gasifying at block 205 may be carried out at a weight-based oxygen-to-hydrocarbon ratio of 0.5 to 10 and all ranges and values there between, including 0.5 to 1, 1 to 2, 2 to 3, 3 to 4, 4 to 5, 5 to 6, 6 to 7, 7 to 8, 8 to 9, and 9 to 10. In embodiments of the invention, synthesis gas stream 23 may comprise 30 to 90 wt. % carbon monoxide and 0.5 to 10 wt. % hydrogen.

In embodiments of the invention, as shown in block 206, method 200 may further comprise reacting carbon monoxide and hydrogen of synthesis gas stream 23 in the presence of a catalyst under reaction conditions sufficient to produce methanol(methanol stream 24). In embodiments of the invention, synthesis gas stream 23 may be purified and the carbon monoxide-to-hydrogen molar ratio of synthesis gas stream 23 may be adjusted before reacting at block 206. In embodiments of the invention, the adjusted hydrogen-to-carbon monoxide molar ratio at block 206 may be in a range of 1 to 10 and all ranges and values there between, including 1 to 2, 2 to 3, 3 to 4, 4 to 5, 5 to 6, 6 to 7, 7 to 8, 8 to 9, and 9 to 10. According to embodiments of the invention, the reaction conditions at block 206 may include a reaction temperature of 100 to 400° C. and all ranges and values there between, including 100 to 125° C., 125 to 150° C., 150 to 175° C., 175 to 200° C., 200 to 225° C., 225 to 250° C., 250 to 275° C., 275 to 300° C., 300 to 350° C., 350 to 375° C., and 375 to 400° C. The reaction conditions at block 206 may further include a reaction pressure of 10 to 100 bar and all ranges and values there between, including 10 to 20 bar, 20 to 30 bar, 30 to 40 bar, 40 to 50 bar, 50 to 60 bar, 60 to 70 bar, 70 to 80 bar, 80 to 90 bar, and 90 to 100 bar. The reaction conditions at block 206 may further include a weight hourly space velocity of 1 to 25000 $hr^{-1}$ and all ranges and values there between, including 1 to 2500 $hr^{-1}$, 2500 to 5000 $hr^{-1}$, 5000 to 7500 $hr^{-1}$, 7500 to 10000 $hr^{-1}$, 10000 to 12500 $hr^-$, 12500 to 15000 $hr^{-1}$, 15000 to 17500 $hr^{-1}$, 17500 to 20000 $hr^{-1}$, 20000 to 22500 $hr^{-1}$, and 22500 to 25000 $hr^{-1}$.

In embodiments of the invention, as shown in block 207, method 200 may further include removing butadiene from $C_4$ hydrocarbon mixture stream 16 in butadiene unit 108 to produce $C_4$ raffinate stream 26 comprising isobutylene. In embodiments of the invention, $C_4$ raffinate stream 26 may comprise 10 to 75 wt. % isobutylene and all ranges and values there between, including 10 to 15 wt. %, 15 to 20 wt. %, 20 to 25 wt. %, 25 to 30 wt. %, 30 to 35 wt. %, 35 to 40 wt. %, 40 to 45 wt. %, 45 to 50 wt. %, 50 to 55 wt. %, 55 to 60 wt. %, 60 to 65 wt. %, 65 to 70 wt. %, and 70 to 75 wt. %. In embodiments of the invention, removing at block 207 may include solvent extraction, extractive distillation, or combinations thereof.

According to embodiments of the invention, as shown in block 208, method 200 may further include reacting isobutylene of $C_4$ raffinate stream 26 with methanol of methanol stream 24 in the presence of a catalyst under reaction conditions sufficient to produce MTBE(methyl tert-butyl ether) forming MTBE stream 27 and unreacted $C_4$ stream 28. In embodiments of the invention, the reaction conditions at block 208 may include a reaction temperature of 40 to 100° C. and all ranges and values there between, including 40 to 50° C., 50 to 60° C., 60 to 70° C., 70 to 80° C., 80 to 90° C., and 90 to 100° C. The reaction conditions at block 208 may further include a reaction pressure of 5 to 40 bar and all ranges and values there between, including 50 to 10 bar, 10 to 15 bar, 15 to 20 bar, 20 to 25 bar, 25 to 30 bar, 30 to 35 bar, and 35 to 40 bar. In embodiments of the invention, the isobutylene-to-methanol ratio at block 208 may be in a range of 0.1 to 10 and all ranges and values there between, including 0.1 to 1, 1 to 2, 2 to 3, 3 to 4, 4 to 5, 5 to 6, 6 to 7, 7 to 8, 8 to 9, and 9 to 10. In embodiments of the invention, the isobutylene at block 208 may be converted at a conversion rate of 75 to 99.9% and all ranges and values there between, including 75 to 80%, 80 to 85%, 85 to 90%, 90 to 95%, and 95 to 99.9%. According to embodiments of the invention, unreacted $C_4$ stream 28 may comprise 1-butene, 2-butene, n-butane, isobutane, unreacted isobutylene, or combinations thereof. In embodiments of the invention, 2-butene of unreacted $C_4$ stream 28 may further react with ethylene to produce propylene via metathesis. Isobutane and n-butane of unreacted $C_4$ stream 28 may be recycled to steam cracking unit 102.

Although embodiments of the present invention have been described with reference to blocks of FIG. 2, it should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2.

In the context of the present invention, at least the following 15 embodiments are described. Embodiment 1 is a method of producing olefins. The method includes distilling a feedstock containing crude oil to produce a plurality of distilling product streams including a naphtha stream and a vacuum residue stream. The method also includes steam cracking the naphtha stream to produce a plurality of cracking product streams containing a $C_2$ to $C_3$ olefins stream, a mixed $C_4$ hydrocarbon stream, and a pyrolysis oil stream. The method further includes hydrocracking the vacuum residue stream to produce a distillate stream having a boiling range less than the vacuum residue stream and a heavy unconverted oil stream having a boiling range higher than the vacuum residue stream. In addition, the method includes deasphalting the heavy unconverted oil stream and the pyrolysis oil from steam-cracking with a solvent to produce a deasphalted oil stream and a pitch stream. Embodiment 2 is the method of embodiment 1, further including gasifying the pitch stream to produce a synthesis gas stream. Embodiment 2 is the method of embodiment 2, further including reacting carbon monoxide and hydrogen of the synthesis gas stream in the presence of a catalyst under reaction conditions sufficient to produce methanol. Embodiment 4 is the method of embodiment 3, wherein, before the reacting step, the synthesis gas stream is purified and a ratio of hydrogen to carbon monoxide in the synthesis gas is adjusted to be in a range of 1 to 10. Embodiment 5 is the method of either of embodiments 3 or 4, wherein the catalyst contains metals or their oxides such as copper, zinc and other transitions metals combined with solid support such as aluminas, silicates, or combinations thereof. Embodiment 6 is the method of any of embodiments 3 to 5, wherein the reaction conditions include a reaction temperature in a range of 100 to 400° C. Embodiment 7 is the method of any of embodiments 3 to 6, wherein the reaction conditions include a reaction pressure in a range of 10 to 100 bar. Embodiment 8 is the method of any of embodiments 3 to 7, further including removing butadiene from the mixed $C_4$ hydrocarbon stream produced by the steam cracking step to produce a $C_4$ raffinate stream comprising at least some isobutylene and reacting isobutylene of the $C_4$ raffinate stream with the methanol produced from the synthesis gas stream to produce at least some methyl tert-butyl ether (MTBE). Embodiment 9 is the method of any of embodiments 1 to 8, wherein the hydrocracking is carried out at a temperature of 300 to 500° C. Embodiment 10 is the method of any of embodiments 1 to 9, wherein the hydrocracking is carried out at a pressure of 10 to 250 bar. Embodiment 11 is the method of any of embodiments 1 to 10, wherein the hydrocracking is carried out in the presence of a catalyst containing transition metals, or metal sulfides with the solid support such as alumina, silica, alumina-silica, magnesia and zeolites, or combinations thereof. Embodiment 12 is the method of any of embodiments 1 to 11, wherein the distillate stream produced in hydrocracking contains hydrocarbons having a boiling range of light distillate, hydrocarbons having a boiling range of middle distillate, hydrocarbons having a boiling range of vacuum gas oil, or combinations thereof. Embodiment 13 is the method of any of embodiments 1 to 12, further including hydrocracking the deasphalted oil under reaction conditions to produce a plurality of streams comprising LPG, naphtha, middle distillates, gasoil, or combinations thereof. Embodiment 14 is the method of embodiment 13, wherein the hydrocracking of deasphalted oil and the vacuum residue are carried out in the same hydrocracking unit. Embodiment 15 is the method of any of embodiments 1 to 14 wherein the steam cracking is carried out at a temperature of 750 to 950° C., a steam to hydrocarbon ratio of 0.1 to 1, and a residence time of 50 to 1000 ms.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of producing olefins, the method comprising:
   distilling a feedstock comprising crude oil to produce a plurality of distilling product streams comprising a naphtha stream and a vacuum residue stream;
   steam cracking the naphtha stream to produce a plurality of cracking product streams comprising a $C_2$ to $C_3$ olefins stream, a mixed $C_4$ hydrocarbon stream, and a pyrolysis oil stream;
   hydrocracking the vacuum residue stream to produce a distillate stream having a boiling range less than the vacuum residue stream and a heavy unconverted oil stream having a boiling range higher than the vacuum residue stream; and
   deasphalting the heavy unconverted oil stream and the pyrolysis oil from steam-cracking with a solvent to produce a deasphalted oil stream and a pitch stream.

2. The method of claim 1, further comprising gasifying the pitch stream to produce a synthesis gas stream.

3. The method of claim 2, further comprising reacting carbon monoxide and hydrogen of the synthesis gas stream in the presence of a catalyst under reaction conditions sufficient to produce methanol.

4. The method of claim 3, wherein, before the reacting step, the synthesis gas stream is purified and a molar ratio of hydrogen to carbon monoxide in the synthesis gas is adjusted to be in a range of 1 to 10.

5. The method of claim 3, wherein the catalyst comprises metals including copper, zinc, other transitions metals, and/or oxides thereof combined with solid support including alumina, silicates, or combinations thereof.

6. The method of claim 3, wherein the reaction conditions include a reaction temperature in a range of 100 to 400° C.

7. The method of claim 3, wherein the reaction conditions include a reaction pressure in a range of 10 to 100 bar.

8. The method of claim 3, further comprising:
   removing butadiene from the mixed $C_4$ hydrocarbon stream produced by the steam cracking step to produce a $C_4$ raffinate stream comprising at least some isobutylene; and
   reacting isobutylene of the $C_4$ raffinate stream with the methanol produced from the synthesis gas stream to produce at least some methyl tert-butyl ether (MTBE).

9. The method of claim 1, wherein the hydrocracking is carried out at a temperature of 300 to 500° C.

10. The method of claim 1, wherein the hydrocracking is carried out at a pressure of 10 to 250 bar.

11. The method of claim 1, wherein the hydrocracking is carried out in the presence of a catalyst comprising transition metals, or metal sulfides thereof with a solid support including alumina, silica, alumina-silica, magnesia and zeolites, or combinations thereof.

12. The method of claim 1, wherein the distillate stream produced in hydrocracking comprises hydrocarbons having a boiling range of light distillate, hydrocarbons having a boiling range of middle distillate, hydrocarbons having a boiling range of vacuum gas oil, or combinations thereof.

13. The method of claim 1, further comprising:
   hydrocracking the deasphalted oil under reaction conditions to produce a plurality of streams comprising LPG (liquefied petroleum gas), naphtha, middle distillates, gasoil, or combinations thereof.

14. The method of claim 13, wherein the hydrocracking of deasphalted oil and the vacuum residue are carried out in the same hydrocracking unit.

15. The method of claim 1, wherein the steam cracking is carried out at a temperature of 750 to 950° C., a steam to hydrocarbon weight ratio of 0.1 to 1, and a residence time of 50 to 1000 ms.

16. The method of claim 4, wherein the catalyst comprises metals including copper, zinc, other transitions metals, and/or oxides thereof combined with solid support including alumina, silicates, or combinations thereof.

17. The method of claim 14, wherein the steam cracking is carried out at a temperature of 750 to 950° C., a steam to hydrocarbon weight ratio of 0.1 to 1, and a residence time of 50 to 1000 ms.

18. The method of claim 13, wherein the steam cracking is carried out at a temperature of 750 to 950° C., a steam to hydrocarbon weight ratio of 0.1 to 1, and a residence time of 50 to 1000 ms.

19. The method of claim 12, wherein the steam cracking is carried out at a temperature of 750 to 950° C., a steam to hydrocarbon weight ratio of 0.1 to 1, and a residence time of 50 to 1000 ms.

20. The method of claim 11, wherein the steam cracking is carried out at a temperature of 750 to 950° C., a steam to hydrocarbon weight ratio of 0.1 to 1, and a residence time of 50 to 1000 ms.

\* \* \* \* \*